United States Patent [19]

Rönnberg et al.

[11] Patent Number: 5,735,838
[45] Date of Patent: Apr. 7, 1998

[54] DISPOSABLE DIAPER HAVING ELASTICIZED LEG CUFFS

[75] Inventors: Peter Rönnberg, Mölndal; Lennart Nilsson, Skärhamn, both of Sweden

[73] Assignee: Molnlycke AB, Gothenburg, Sweden

[21] Appl. No.: 637,689

[22] PCT Filed: Nov. 14, 1994

[86] PCT No.: PCT/SE94/01064

§ 371 Date: Jun. 20, 1996

§ 102(e) Date: Jun. 20, 1996

[87] PCT Pub. No.: WO95/13781

PCT Pub. Date: May 26, 1995

[30] Foreign Application Priority Data

Nov. 15, 1995 [SE] Sweden ............................ 9303746

[51] Int. Cl.⁶ ............................................. A61F 13/15
[52] U.S. Cl. ................................. 604/385.2; 604/391
[58] Field of Search .......................... 604/373, 385.1, 604/385.2, 386, 387, 389–391, 393, 392, 397, 398

[56] References Cited

U.S. PATENT DOCUMENTS

| | | |
|---|---|---|
| 4,050,462 | 9/1977 | Woon et al. |
| 4,437,860 | 3/1984 | Sigl et al. |
| 4,486,192 | 12/1984 | Sigl . |
| 4,904,251 | 2/1990 | Igave et al. ............ 604/385.2 |
| 5,176,671 | 1/1993 | Roessler et al. ........... 604/386 |
| 5,454,803 | 10/1995 | Sayeser et al. .......... 604/385.2 |
| 5,476,458 | 12/1995 | Glaug et al. ............ 604/385.2 |

FOREIGN PATENT DOCUMENTS

| | | |
|---|---|---|
| 167170 B1 | 10/1986 | Denmark . |
| 0532034 | 3/1993 | European Pat. Off. ......... 604/392 |
| 271521 | 5/1990 | Japan . |
| 2103093 | 2/1983 | United Kingdom . |
| 2262873 | 7/1993 | United Kingdom . |
| WO 93/10733 | 6/1993 | WIPO . |
| WO 93/21877 | 11/1993 | WIPO . |

*Primary Examiner*—John G. Weiss
*Assistant Examiner*—K. M. Reichle
*Attorney, Agent, or Firm*—Burns, Doane Swecker & Mathis LLP

[57] ABSTRACT

A disposable diaper in which elastic which provides elasticized leg cuffs is accommodated in a pocket of material formed by either a facing sheet or a backing sheet of the diaper. The pocket extends along each longitudinal edge portion of the diaper. Fastening member for fastening the diaper around a wearer are affixed to the diaper between the facing sheet and the backing sheet.

10 Claims, 4 Drawing Sheets

5,735,838

DISPOSABLE DIAPER HAVING ELASTICIZED LEG CUFFS

TECHNICAL FIELD

The present invention relates to a disposable diaper, and, more particularly, to a disposable diaper having elasticized leg cuffs.

BACKGROUND OF THE INVENTION

Disposable diapers with elasticized leg cuffs are known in the art. Whilst it is advantageous that the elastic material provides a retractive force in the leg cuffs, for reasons of comfort, it is desirable that no retractive forces be applied to the waist portions of the diaper.

From U.S. Pat. No. 4,486,192, it is known to treat the free ends of elastic material in the waist portions of a diaper to destroy their elastic properties. This may be achieved by subjecting the ends of the elastic material to heat to thereby "kill" the elastic properties of the material. A disposable diaper is disclosed in U.S. Pat. No. 4,437,860 in which uniformally stretched elastic bands are adhesively bonded along the entire length of both longitudinal edges of the diaper. Heavier concentrations of adhesive are provided in the waist portions than in the crotch portion to reduce gathering and creep of the elastic in the waist portions.

SUMMARY OF THE INVENTION

It is an object of the present invention to provide an absorbent article such as a disposable diaper which lends itself to mass production techniques and in which the elastic material which provides a retractive force in the leg cuffs is so arranged that means for fastening the diaper around a wearer can be simply and effectively affixed to the diaper.

This object is achieved in accordance with the present invention by a disposable diaper having an absorbent core disposed between a facing sheet and backing sheet. The diaper has a generally hour glass shape with a narrow centrally disposed crotch portion and wider waist portions at transverse end regions of the crotch portion. The waist portions are provided with means for fastening the diaper around a wearer. The diaper also includes prestretched elastic means disposed along longitudinal edge portions of the diaper for providing predetermined gathered and substantially non-gathered regions along the edge portions, with substantially non-gathered regions being provided at said waste portions. The elastic means are enclosed with a pocket along each of the longitudinal edge portions, and the pocket is formed by one of the sheets with the elastic means being adhered to the pocket at the gathered regions and non-adhered at the non-gathered regions. The means for fastening the diaper are affixed to the waist portions between the pocket and the other of the sheets.

Preferred embodiments of the present invention are detailed in the dependent claims.

BRIEF DESCRIPTION OF THE DRAWINGS

The invention will be described in greater detail in the following by way of example only and with reference to the attached drawings, in which.

DETAILED DESCRIPTION OF PREFERRED EMBODIMENTS

Figure 1:
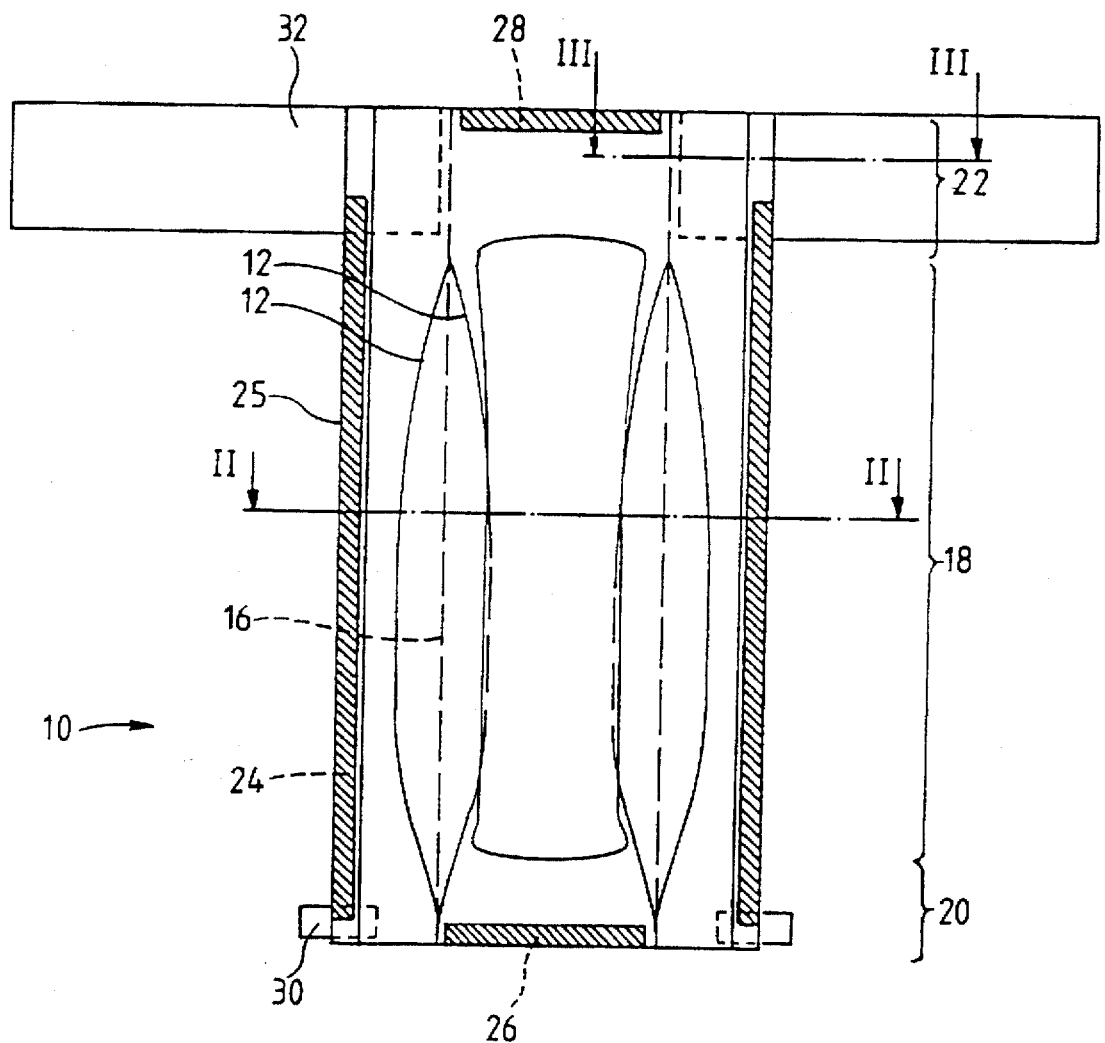
FIG. 1 is a plan view of an absorbent article in accordance with the present invention having elasticized leg cuffs, the article being illustrated during a stage of the manufacturing process.

In the drawings, an absorbent article in the form of a disposable diaper is generally denoted by reference numeral 10. For reasons of clarity, the diaper 10 is shown in FIG. 1 in a stage occupied by the diaper during its manufacture. Accordingly, reference numeral 12 denotes joining lines, for example glue lines or heat bonding lines, about which the diaper is gathered in a manner known per se to form a pair of inner cuffs 14 (FIG. 2) through which an elastic chord 16 runs. Due to the gathering of the diaper about the joining lines 12, the diaper adopts a generally hour glass shape with a narrow centrally disposed crotch portion 18 and wider waist portions 20, 22 at transverse end regions of the crotch portion.

In accordance with the invention, the diaper 10 is provided with prestretched elastic means 24 disposed along longitudinal edge portions 25 of the diaper. Advantageously, the waist portions 20, 22 may be provided with transversely extending elastic means 26, 28 respectively.

To permit the diaper to be fastened around a wearer, fastening means are provided at the waist portions. As illustrated in FIG. 1, the waist portion 20 which would normally be disposed at the front of the wearer may be provided with a pair of fastening means such as hook members 30, with each hook member 30 extending from the longitudinal edge portion 25 of the diaper. The fastening means may further comprise a belt 32 extending from the waist portion 22 which portion, during use, is normally disposed at the back of the wearer. As illustrated in FIG. 1, the belt may be in two halves, with each half extending from the opposed longitudinal edge portions 25 of the diaper. The two belt halves are intended to pass around the waist of the wearer and are fastened together at the front of the wearer by any suitable means such as a hook and loop fastener. Preferably, the belt is made from a nonwoven material which acts as a loop fastener for the hook members 30.

Figure 2:
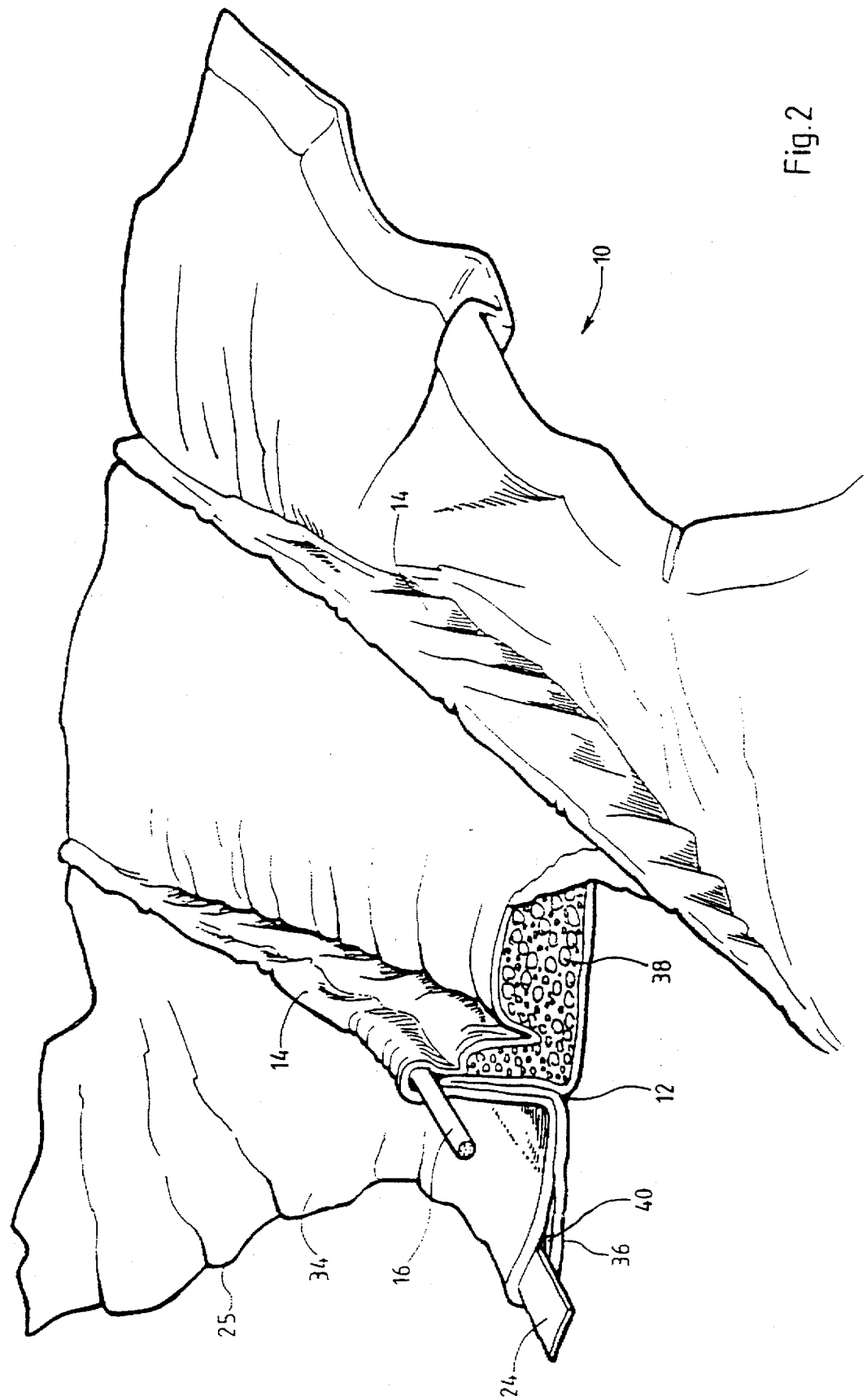
FIG. 2 is a partial sectional perspective view taken substantially along the line II—II of FIG. 1, with the article in a finished condition.

The structure of the diaper of FIG. 1 will be more easily understood from the partial sectional view through the crotch portion 18, as illustrated in FIG. 2. In keeping with the present invention, the diaper 10 has a generally hour glass shape and includes a facing sheet 34, a backing sheet 36 and an absorbent core 38 sandwiched between the facing and backing sheets 34, 36 respectively. The specific components used to form the illustrated diaper may be any of the types commonly used for such purposes. For example, the facing sheet 34 may be any soft flexible liquid permeable material such as a nonwoven fibrous web having a basis weight of around 20 g/m$^2$. The backing sheet 36 is made from a liquid impermeable material such as a thin (for example 20μ) plastic film of polyethylene, polypropylene, polyvinylchloride or the like. The absorbent core 38 may comprise wood pulp fibres, air-laid tissue, various superabsorbent materials, etc.

As mentioned above with reference to FIG. 1, prestretched elastic means 24 are disposed along the longitudinal edge portions 25 of the diaper. As clearly shown in FIG. 2, the elastic means 24 may be in the form of an elongate elastic band. The elastic band is preferably relatively wide, for example between 1 and 2 cm, preferably about 1.5 cm, so as to reduce the tendency for the leg cuff to mark the wearer.

Figure 3:
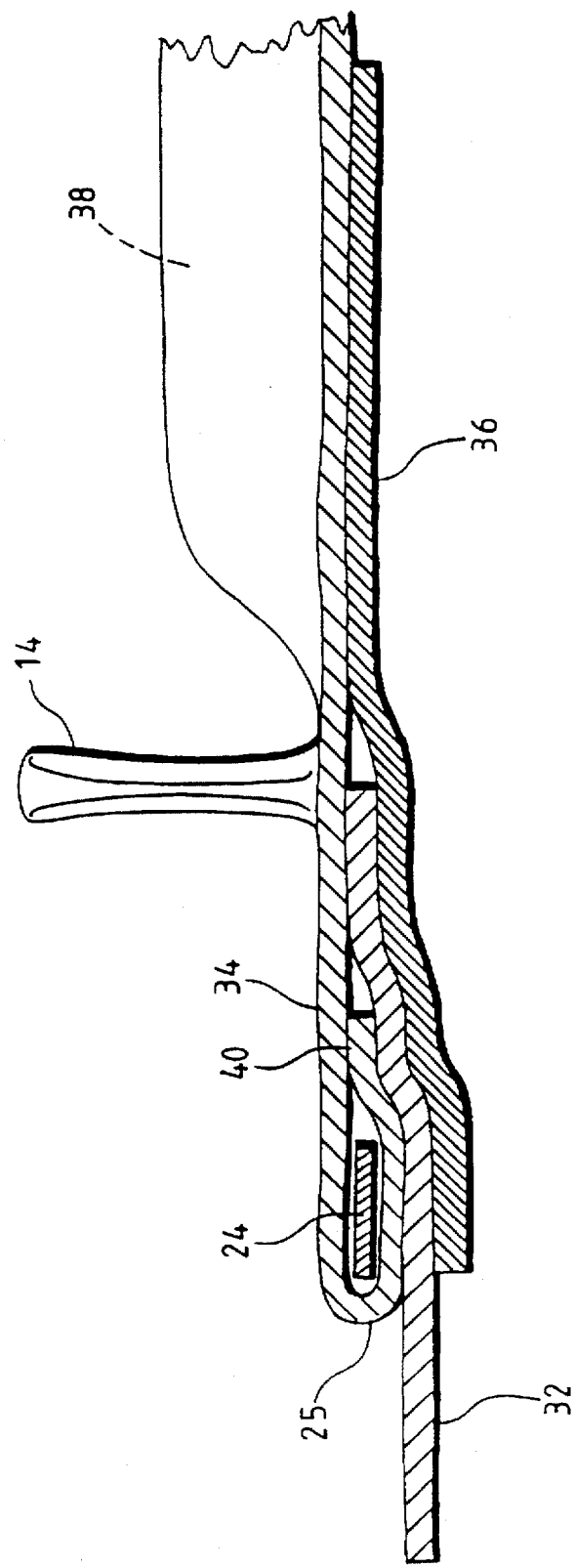
FIG. 3 is a sectional view substantially along the line III—III of FIG. 1.

The arrangement of the elastic means 24 along the longitudinal edge portions 25 of the diaper will now be described with particular reference to FIGS. 3 and 4. In accordance with the present invention, the elastic means 24 are enclosed within a pocket along each of the longitudinal edge portions 25 of the diaper. In FIG. 3, the pocket is formed by the facing sheet 34. More particularly, the facing sheet 34 presents a longitudinal free edge portion 40 which is folded under and adhered to the underside of the facing sheet to thereby form a pocket within which the elastic means 24 is accommodated. The pocket advantageously extends along the entire longitudinal edge portion 25 of the diaper and the elastic band 24 is adhered to the material forming the pocket at those regions along the longitudinal edge portion 25 at which gathering of the facing sheet is desired, for example in the crotch portion 18 where the longitudinal edge portions 25 form leg cuffs (see for example FIG. 2). Where no gathering is desired, for example in the waist portions 20, 22, the elastic band remains unadhered to the pocket. Thus, in FIG. 3, which represents a sectional view through the waist portion 22, the elastic band 24 is not adhered to the material of the pocket in the waist portion.

Figure 4:
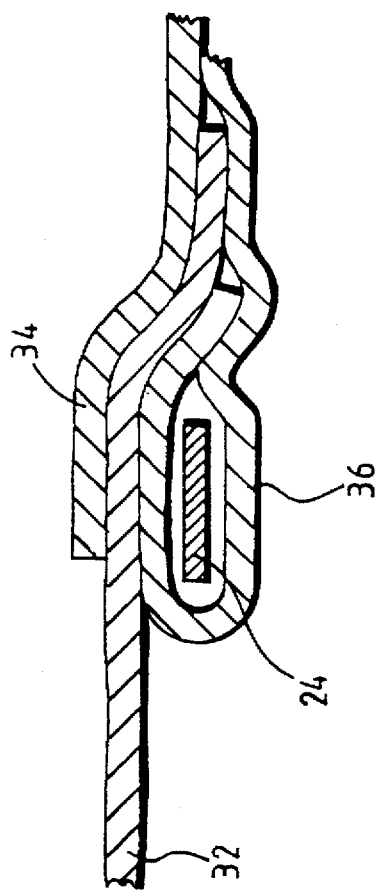
FIG. 4 is a sectional view corresponding essentially to that of FIG. 3, illustrating a further embodiment of the absorbent article according to the invention.

FIG. 4 corresponds essentially to FIG. 3 with the exception that the pocket for the elastic band 24 is formed by the backing sheet 36. Similarly, where gathering is desired the elastic band is adhered to the material forming the pocket, whilst no adherence is present at regions at which no gathering is required.

The above-described arrangement of the elastic means 24 within a pocket allows for simple attachment of the fastening means 30, 32 to the waist portions 20, 22 respectively. As illustrated in FIG. 3, the fastening means, in this case the belt 32, is inserted between the backing sheet 36 and the pocket formed by the facing sheet 34 and adhered in place. In order to provide a large adhered surface area, the belt advantageously extends into the diaper between the facing sheet and the backing sheet substantially up to the inner cuff 14. The fastening means 32 illustrated in FIG. 4 is affixed to the diaper in a corresponding manner.

The present invention is not restricted to the embodiments described above and illustrated by way of example in the drawings, but may be varied within the scope of the appended claims. For example, the sheet which does not form the pocket need not extend up to the longitudinal edge portion of the diaper, but may instead terminate nearer the inner cuff. It is to be understood that the term "diaper" is intended to encompass absorbent articles of the type disclosed in the appended claims which are worn by infants and adults alike.

We claim:

1. A disposable diaper comprising: an absorbent core disposed between and secured to a facing sheet and backing sheet, a transverse direction and a longitudinal direction said diaper having a generally hourglass shape with a narrow centrally disposed crotch portion and wider waist portions at transverse end regions of said crotch portion, said waist portions being provided with means for fastening the diaper around a wearer, said diaper further having prestretched elastic means disposed along longitudinal edge portions of said diaper for providing predetermined gathered and substantially non-gathered regions along said edge portions, with substantially non-gathered regions being provided at said waist portions, wherein said elastic means are enclosed within a pocket along each of said longitudinal edge portions, said pocket being formed by one of said sheets with said elastic means being adhered to said pocket at said gathered regions and non-adhered at said non-gathered regions, and said means for fastening the diaper being affixed to said waist portions between said pocket and the other of said sheets.

2. The disposable diaper according to claim 1, wherein said pocket is formed by said facing sheet.

3. The disposable diaper according to claim 2, wherein said facing sheet is made from a nonwoven material.

4. The disposable diaper according to claim 1, wherein said pocket is formed by said backing sheet.

5. The disposable diaper according to claim 1, wherein said backing sheet is made from a liquid impermeable material.

6. The disposable diaper according to claim 1, wherein said means for fastening the diaper around a wearer includes a belt, said belt having two halves with each half extending from a longitudinal edge portion of one of said waist portions.

7. The disposable diaper according to claim 6, wherein said belt is made from a nonwoven material.

8. The disposable diaper according to claim 6, wherein said means for fastening the diaper around a wearer further includes a pair of hook members, with each hook member extending from a longitudinal edge portion of the other of said waist portions.

9. The disposable diaper according to claim 6, wherein the diaper is provided with a pair of inner cuffs extending longitudinally along the diaper in at least the crotch portion, and in that said belt halves project into the diaper between the facing sheet and the backing sheet substantially up to said inner cuffs.

10. The disposable diaper according to claim 1, wherein said pockets extend along the entire longitudinal edge portions of said diaper.

* * * * *